United States Patent
Hutter, III

(10) Patent No.: US 7,389,698 B2
(45) Date of Patent: Jun. 24, 2008

(54) NUTPLATE BOND STRENGTH TESTER UNIT

(75) Inventor: Charles G. Hutter, III, Carson City, NV (US)

(73) Assignee: Physical Systems, Inc., Carson City, NV (US)

(*) Notice: Subject to any disclaimer, the term of this patent is extended or adjusted under 35 U.S.C. 154(b) by 115 days.

(21) Appl. No.: 11/458,028

(22) Filed: Jul. 17, 2006

(65) Prior Publication Data

US 2007/0044569 A1 Mar. 1, 2007

Related U.S. Application Data

(60) Provisional application No. 60/711,168, filed on Aug. 24, 2005.

(51) Int. Cl.
*G01N 3/08* (2006.01)
(52) U.S. Cl. .......................... 73/827; 73/150 A; 73/826; 73/841; 73/842; 73/846; 228/103
(58) Field of Classification Search ............... 73/150 A, 73/826, 827, 841, 842, 846; 228/103
See application file for complete search history.

(56) References Cited

U.S. PATENT DOCUMENTS

| | | | | |
|---|---|---|---|---|
| 4,822,656 A | * | 4/1989 | Hutter, III | 428/41.8 |
| 5,013,391 A | | 5/1991 | Hutter, III et al. | |
| 5,671,634 A | * | 9/1997 | Donovan | 73/150 A |
| 5,704,747 A | * | 1/1998 | Hutter et al. | 411/70 |
| 6,092,427 A | * | 7/2000 | Hunt et al. | 73/835 |
| 6,282,950 B1 | * | 9/2001 | Taylor et al. | 73/150 A |
| 6,612,184 B1 | * | 9/2003 | Hollingsworth et al. | 73/827 |
| 2007/0141289 A1 | * | 6/2007 | Hutter, III | 428/40.1 |

* cited by examiner

*Primary Examiner*—Edward Lefkowitz
*Assistant Examiner*—Freddie Kirkland, III
(74) *Attorney, Agent, or Firm*—Kelly Lowry & Kelley, LLP; Stuart O. Lowry

(57) ABSTRACT

A bond strength tester unit is provided for testing adhesive bond strength of a nutplate or the like attached to a substrate, such as by adhesive bonded attachment to a blind side of the substrate in substantial alignment with a substrate opening. The nutplate may be constructed according to U.S. Pat. No. 5,013,391, and carries a fastener element such as a threaded nut or the like for subsequent connection with a mating fastener element such as a threaded bolt or the like passed through the substrate opening. The tester unit includes a tool tip having a reaction head for engaging the substrate, in combination with an actuator pin for applying a test force of selected magnitude against the adhesively bonded nutplate. In the event of inadequate bond strength, the actuator pin will separate the nutplate from the substrate.

18 Claims, 6 Drawing Sheets

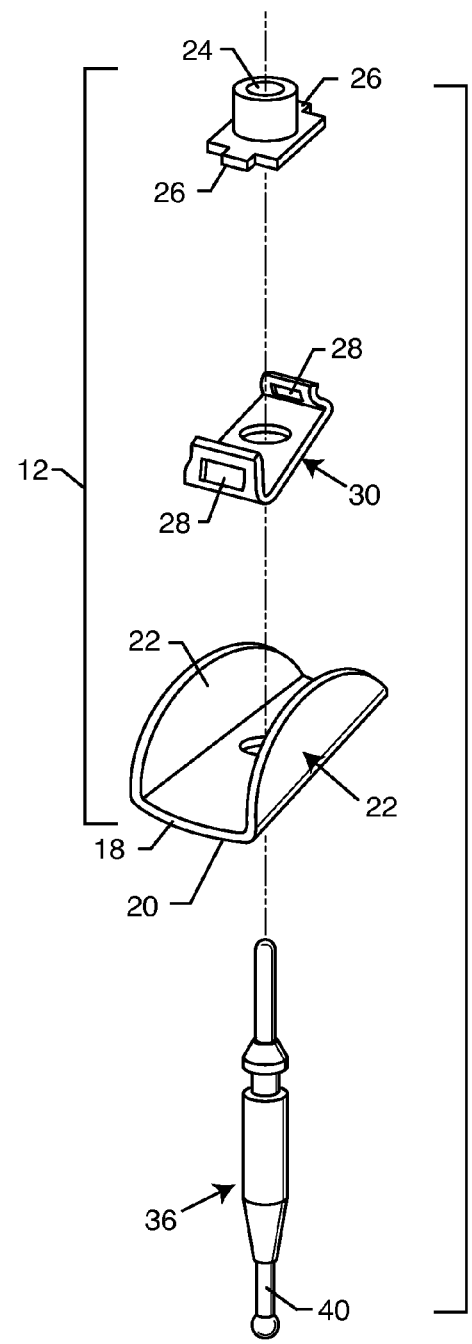
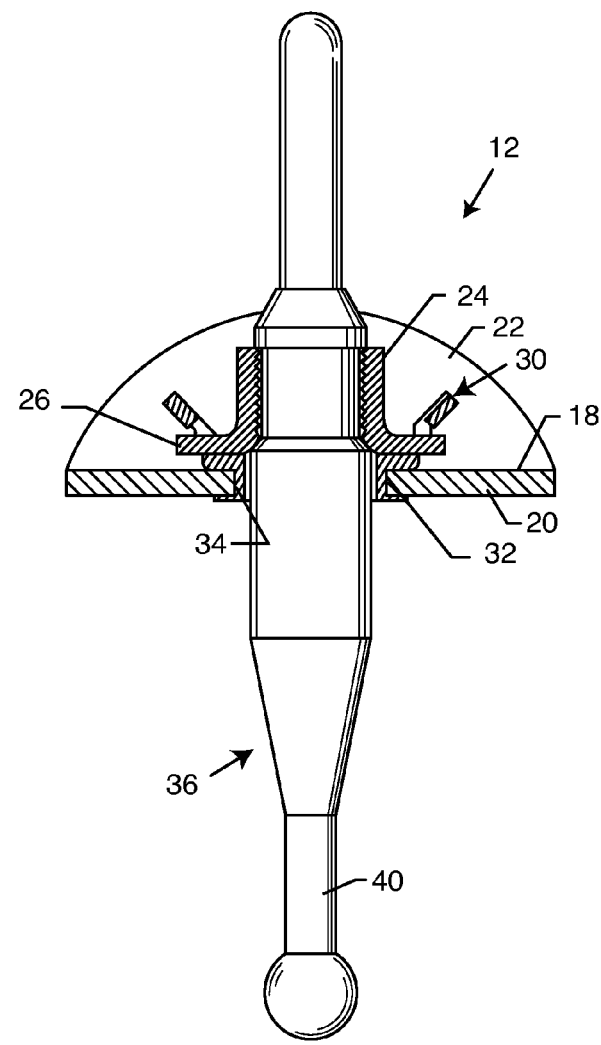
FIG. 3
FIG. 4

NUTPLATE BOND STRENGTH TESTER UNIT

BACKGROUND OF THE INVENTION

This invention relates generally to a system and method for testing and verifying adequate bond strength attachment of an adhesively bonded attachment component such as a nutplate or the like affixed to a selected substrate. More specifically, this invention relates to a bond strength tester unit and method for quickly and easily testing nutplate bond strength attachment, e.g., to a blind side of a substrate. In particular, this invention relates to a bond strength tester unit for use with an adhesive bonded nutplate of the general type disclosed in U.S. Pat. No. 5,013,391.

In many manufacturing environments, it is necessary or desirable to install components onto a blind or reverse side of a supporting substrate. As one common example, nutplates are well known in the automotive and aerospace industries for use in mounting a threaded nut or the like onto the blind side of a supporting substrate, typically in alignment with an access opening formed in the substrate, to accommodate subsequent reception of a mating fastener component such as a threaded screw or bolt. Such nutplates include a fastener element such as a floating or fixed nut carried by a base which is fastened to the substrate normally by means of one or more rivets extending through rivet ports formed in the substrate adjacent the access opening. Alternately, adhesive mounting techniques have been proposed for adhesively bonding the nutplate base onto the substrate, thereby avoiding the need to form the rivet ports. For optimum bond strength, such adhesive mounting techniques require the nutplate to be pressed against the substrate with a positive force during curing of the adhesive material.

U.S. Pat. No. 5,013,391 discloses a nutplate assembly including a nutplate base adapted for adhesive bonding onto a substrate. A fixture pin is included for drawing and retaining the nutplate base with a positive force in a direction seated firmly against the substrate for the duration of a bonding agent cure time. The fixture pin is accessible through the access opening at a front side of the substrate for convenient post-cure removal or separation from the nutplate.

While such adhesive mounted nutplates of the above-described type, installed at the blind side of a substrate, accommodate quick and easy subsequent assembly with a mating fastener element, problems can arise when the bond strength is inadequate to support a subsequent load during normal use. That is, in the event of nutplate loading with a force exceeding the adhesive bond strength, the nutplate can separate and fall away from the substrate. When this failure mode occurs following normal substrate installation in an arrangement which renders the blind side of the substrate substantially inaccessible, remedial action can require time-consuming and labor-intensive substrate disassembly from adjoining structures, e.g., such as adjacent substrate panels and frame components in an aircraft or the like.

There exists, therefore, a significant need for a system and method for quickly and easily confirming adequate bond strength attachment of a nutplate to a substrate, and for identifying any inadequately bonded nutplates to permit replacement thereof prior to subsequent manufacturing steps rendering the substrate blind side substantially inaccessible. The present invention fulfills these needs and provides further related advantages.

SUMMARY OF THE INVENTION

In accordance with the invention, a bond strength tester unit and method are provided for testing adhesive bond strength of an attachment component such as a nutplate or the like attached to a substrate, such as by adhesive bonded attachment to a blind side of the substrate in substantial alignment with an access opening formed in the substrate. The tester unit comprises a tool tip having a reaction head for engaging the substrate, in combination with an actuator member for applying a selected test force to the adhesively bonded nutplate. In the event of inadequate adhesive bond strength in response to the applied test force, the nutplate will separate from the substrate.

The bond strength tester unit and method of the present invention are particularly designed for use with an adhesively bonded nutplate of the general type shown and described in U.S. Pat. No. 5,013,391, which is incorporated by reference herein. Such nutplate comprises a nutplate base adapted for adhesive bonded attachment to the substrate such as at a blind side thereof, a fastener element such as a threaded nut or the like carried by the nutplate base and adapted for subsequent connection, e.g., with a mating fastener element such as a threaded bolt or the like passed through the access opening from a front side of the substrate. A fixture pin is provided for initially retaining the nutplate base seated against the blind side of the substrate with a positive retention force during curing of a bonding agent. The fixture pin protrudes forwardly through the access opening formed in the substrate for convenient separation from the nutplate and substrate after the bonding agent has cured.

In one preferred form, the tester unit comprises a compact power tool having a tool body with the tool tip protruding forwardly therefrom. The tool tip includes the reaction head having at least one and preferably multiple latch jaws having a size and shape for slide-fit reception through the access port, followed by radial expansion sufficient for locking engagement with the substrate at the blind side thereof. The tool tip further includes the actuator member such as an elongated pusher pin having a sufficiently enlarged tip or cap thereon for engaging and applying a test force of selected magnitude to the adhesively bonded nutplate, as by bearing engagement with the threaded nut carried thereby. In a preferred form, the pusher pin is coaxially positioned within the latch jaws and further includes an elongated shank defining a cam surface thereon for engaging and radially expanding said latch jaws for secure locking engagement with the substrate, upon relative axial advancement of the pin. This cam surface is formed for timed operation whereby the latch jaws lockingly engage with the substrate preferably a short interval before the pusher pin tip or cap applies the selected test force to the bonded nutplate. In one preferred form, the pusher pin is axially advanced relative to the latch jaws. In an alternative preferred form, the latch jaws are axially retracted relative to the pusher pin.

In the event of inadequate bond strength attachment of the nutplate to the substrate, the tester unit will forcibly separate the nutplate from the substrate. Such nutplate separation thus provides a clear indication of insufficient bond strength attachment, and the separated nutplate can be replaced. Conveniently, the tester unit is employed at a early manufacturing phase wherein the substrate blind side is still accessible for quick and easy nutplate replacement. Thereafter, a substrate carrying one or more nutplates which are adhesively bonded thereto each with sufficient bond strength may be assembled with adjoining structural components to render the substrate blind side inaccessible, with little or no risk of subsequent post-assembly nutplate separation from the substrate.

Other features and advantages of the present invention will become apparent from the following more detailed description, taken in connection with the accompanying drawing which illustrate, by way of example, the principals of the present invention.

BRIEF DESCRIPTION OF THE DRAWINGS

The accompanying drawings illustrate the invention. In such drawings:

FIG. 3 is an exploded perspective view illustrating construction details of the nutplate and fixture pin shown in FIG. 2;

FIG. 4 is an enlarged vertical section taken generally on the line 4-4 of FIG. 2;

DETAILED DESCRIPTION OF THE PREFERRED EMBODIMENTS

Figure 1:
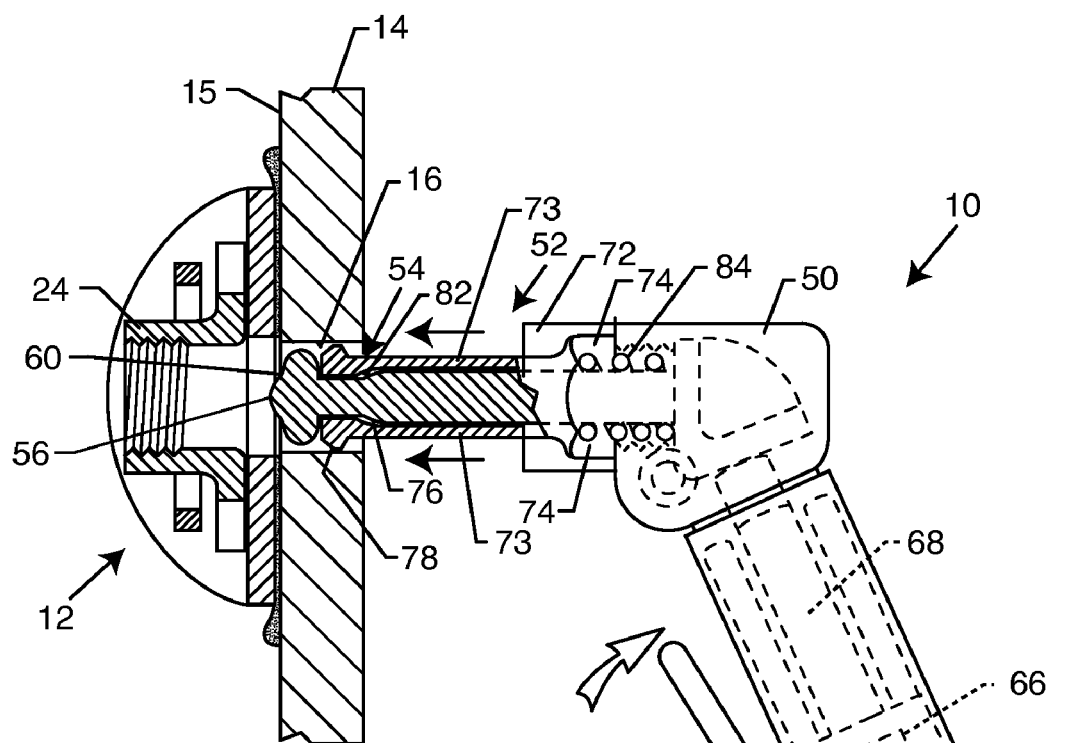
FIG. 1 is a side elevation view, shown partially in vertical section, of a nutplate bond strength tester unit constructed in accordance with one preferred form of the present invention, for use in testing bond or affixation strength of a nutplate of the like mounted onto a blind side of a substrate.
Figure 2:
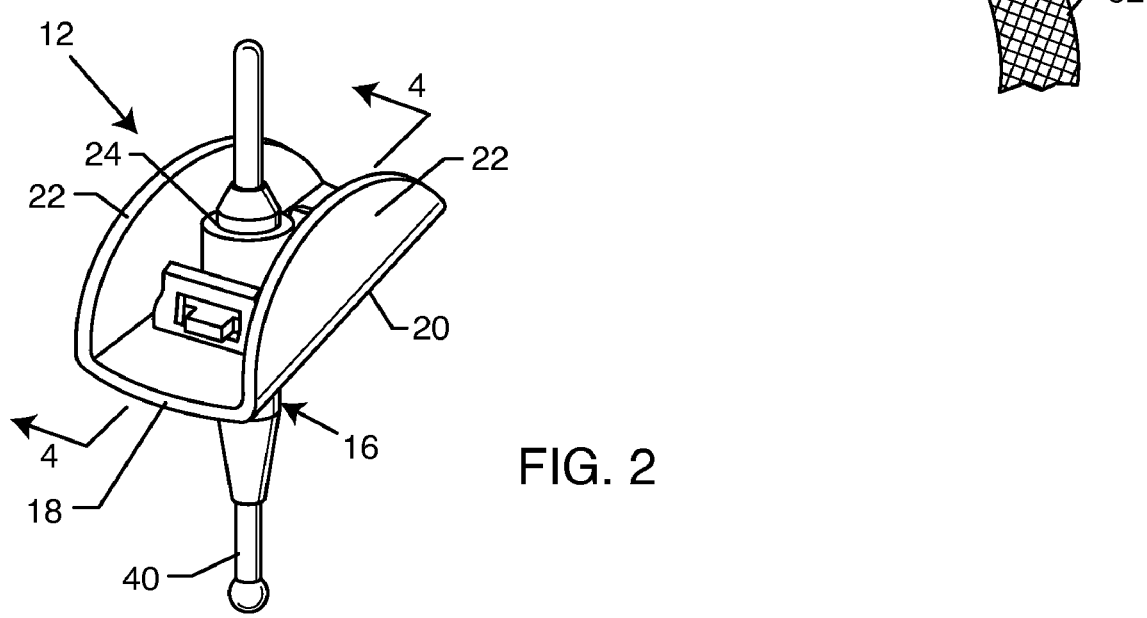
FIG. 2 is a perspective view illustrating an exemplary adhesive mounted nutplate and related fixture pin for mounting onto a substrate.
Figure 5:
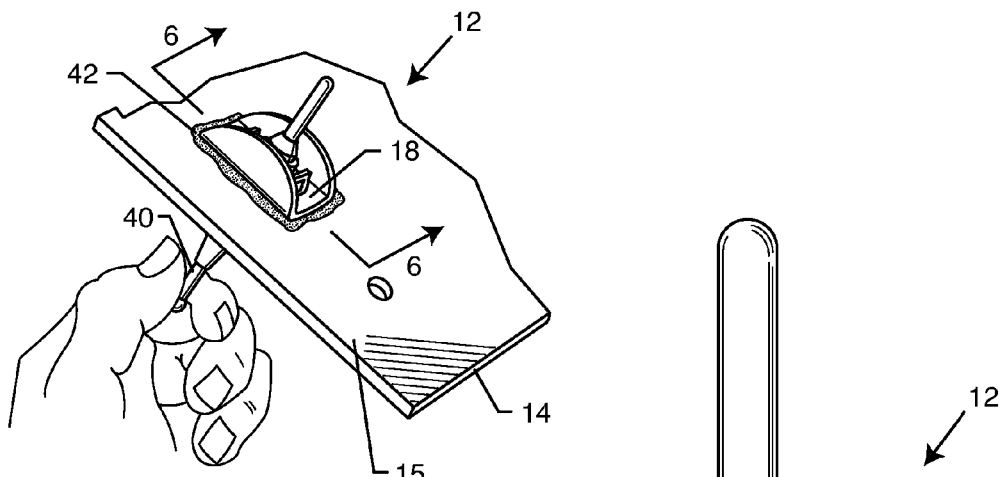
FIG. 5 is a fragmented perspective view illustrating nutplate mounting onto a substrate.
Figure 6:
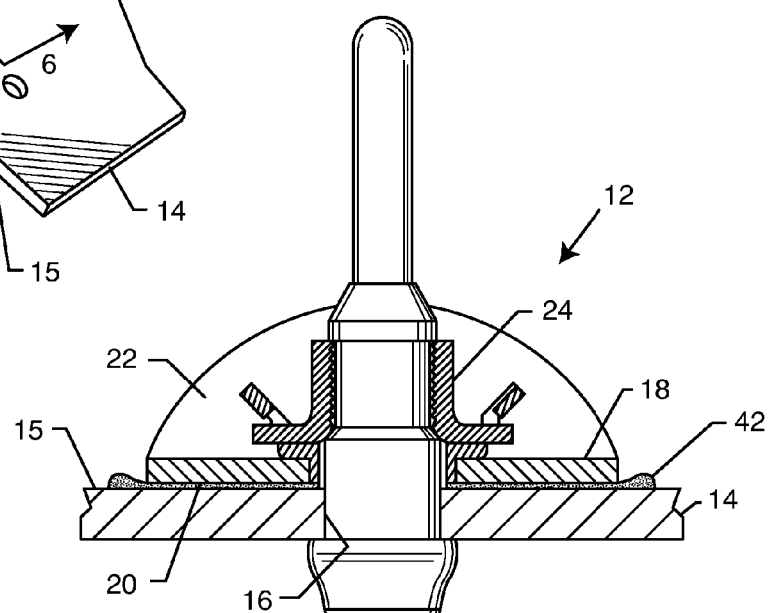
FIG. 6 is an enlarged vertical sectional view taken generally on the line 6-6 of FIG. 5.
Figure 7:
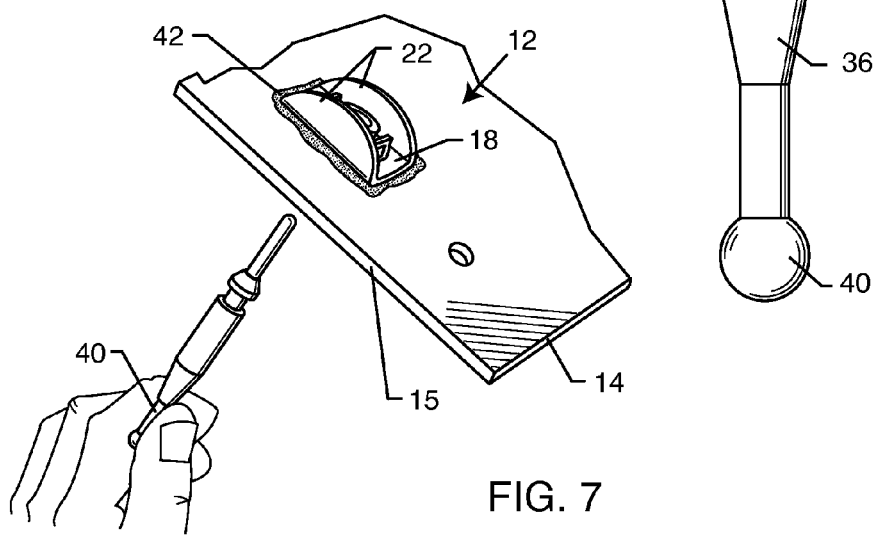
FIG. 7 is a fragmented perspective view similar to FIG. 5, but depicting fixture pin removal from the adhesively mounted nutplate.
Figure 8:
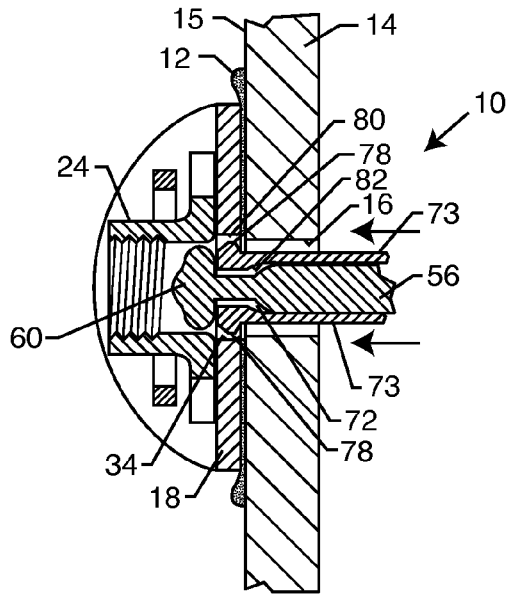
FIG. 8 is a fragmented vertical sectional view similar to a portion of FIG. 1, and showing a tester unit tool tip inserted into a substrate access opening for testing bond strength of a nutplate mounted onto the substrate blind side.

As shown in the exemplary drawings, a bond strength tester unit referred to generally in FIGS. 1 and 8-10 by the reference numeral 10 is provided for testing and confirming adequate adhesive bond strength attachment of an attachment component such as a nutplate or nutplate assembly 12 onto a substrate 14, such as on a rear or blind side 15 of the substrate 14 in substantial alignment with an access opening 16 formed in the substrate. In the normal event of adequate bond strength attachment to the substrate 14, the nutplate 12 will remain in place in response a test force of selected magnitude applied by the tester unit 10. However, in the case of inadequate bond strength, the nutplate 12 will separate from the substrate 14 and thereby indicate a need for a replacement nutplate affixed with adequate bond strength.

The bond strength tester unit 10 of the present invention is particularly useful with a nutplate or nutplate assembly 12 of the general type shown and described in U.S. Pat. No. 5,013,391, which is incorporated by reference herein. Such nutplate or nutplate assembly 12 and related method of adhesive bonded affixation to the substrate 14 is shown in detail in FIGS. 2-7. As shown, a nutplate base 18 defines an underside surface 20 for secure adhesively bonded affixation onto the substrate 14, wherein this substrate base 18 may be formed from a selected metal or non-metal (e.g., composite) material in accordance with bond-on compatibility with the substrate 14. The illustrative drawings show the nutplate base 18 in the form of a generally circular disk having opposite side regions turned upwardly to define a pair of generally parallel upstanding side wings 22 for supporting and retaining a fastener element such as the illustrative internally threaded nut 24. In this regard, the threaded nut 24 includes means for assembly with the nutplate base 18 in a floating or fixed manner, with the illustrative drawings depicting a floating nut arrangement wherein outwardly protruding tabs 26 on the nut 24 movably snap-fit engage with apertures 28 formed in a cage member 30 which is adapted in turn for securement by suitable means to the nutplate base 18. FIG. 4 shows this securement means in the form of a liner sleeve 32 or the like fitted within a central port 34 formed in the nutplate base 18. However, persons skilled in the art will recognize and appreciate that alternative securement methods may be used.

A fixture pin 36 formed from a resilient material is initially fitted through the central port 34 in the nutplate base 18, and further through an aligned port in the cage member 30 to extend into and preferably through the threaded nut 24. This fixture pin 36 includes a variety of different-sized diametric segments as described in more detail in the above-cited U.S. Pat. No. 5,013,391, in combination with an elongated tail 40 extending downwardly or forwardly from the nutplate base 18. In use, an adhesive bonding agent 42 is applied to the underside surface 20 of the nutplate base 18, and the nutplate or nutplate assembly 12 is firmly seated against the blind side 15 of the substrate 14 (FIGS. 5 and 6) with the tail 40 of the fixture pin 36 protruding downwardly or forwardly through the substrate access opening 16 to the front side of the substrate. The tail 40 is pulled downwardly or forwardly with a sufficient force to position an appropriately sized diametric segment of the fixture pin 36 within the substrate access port 16, with a sufficient press-fit or compression force. With this configuration, during an initial cure cycle for the bonding agent 42, the fixture pin 36 functions to pull downwardly or forwardly on the nutplate 12 with a substantially constant force to pull and retain the nutplate 12 in firm seated engagement with the substrate blind side, and with a positive force urging the nutplate 12 toward and firmly against the substrate blind side 15 to achieve a substantially optimized strength bonded interface. When the bonding agent 42 has cured, the tail 40 of the resilient fixture pin 36 at the front side of the substrate 14 can be grasped and pulled with a sufficient force to separate and remove the fixture pin from the nutplate 12, as viewed in FIG. 7. Thereafter, the threaded nut 24 of the blind side-mounted nutplate 12 is accessible through the access opening 16 for threaded connection with a mating fastener member (not shown) such as threaded bolt or screw passed from the substrate front side through the access opening.

The bond strength tester unit 10 is designed for quickly and easily testing the strength of the adhesively bonded attachment of the nutplate 12 to the substrate 14, in a manner that will identify a faulty bonded interface, i.e., inadequate bond strength attachment, by separating the nutplate from the substrate and thereby indicating a need for a replacement nutplate secured with adequate bond strength. In this regard, the bond strength tester unit 10 is normally intended for use following bonded attachment of one or more nutplates 12 to the substrate 14, but prior to subsequent manufacturing steps wherein the substrate is installed or assembled with adjoining structures rendering the substrate blind side substantially inaccessible. That is, any faulty nutplate attachments are identified while the substrate blind side 15 is still accessible, so that such faulty attachments (if present) can be identified and expeditiously replaced.

In accordance with one preferred form as viewed generally in FIG. 1, the tester unit 10 generally comprises a hand-held power tool having a tool body 50 with a forwardly protruding tool tip 52. The tool tip 52 comprises a reaction head 54 in combination with an actuator member 56 such as an elongated pusher pin. In use, the reaction head 54 and the pusher pin 56 are axially reciprocal one relative to the other, whereby the reaction head 54 engages the substrate 14 while a tip or cap 60 on the pusher pin 56 engages and applies a test force of predetermined or selected magnitude to the bonded-on nutplate 12.

More particularly, the tool body 50 is coupled to a suitable source of drive power, such as by connection to a compressed air supply (not shown) by means of a pneumatic hose 62 or the like. FIG. 1 shows a trigger lever 64 mounted on the tool body 50 for selectively coupling the compressed air source to a pneumatic drive cylinder unit 66 for appropriately displacing a drive ram 68. This drive ram 68 is linked to a rear end of the elongated pusher pin 56 which protrudes from a front or nose end 72 of the tool body 50. As shown, the pusher pin 56 includes an elongated shank of relatively narrow cross sectional size and shape for reciprocal sliding movement generally coaxially within the reaction head 54 which is defined by at least one and preferably a pair of elongated latch arms 73 having enlarged rear or base ends 74 pivotally seated within the nose end 72 of the tool body 50.

When the pusher pin 56 is pneumatically advanced upon depression of the trigger lever 64, a ramped cam surface 76 defined along the pin shank engages and displaces the latch arms 73 of the reaction head 54. In this regard, these latch arms 73 respectively include enlarged distal ends defining a corresponding pair radially outwardly protruding latch jaws 78 having tapered leading and trailing end faces. Prior to depression of the trigger lever 64, and with the pusher pin 56 in a retracted state (FIG. 8), these latch jaws 78 present a diametric size that is sufficiently small for slide-fit reception into and through the substrate access opening 16. The latch arms 73 further provide a sufficient spring characteristic for at least slight radially outward expansion upon reaching the blind side 15 of the substrate 14, within a small blind side chamber 80 defined by the port 34 in the nutplate base 18, so that the latch jaws 78 expand radially for initial locking engagement against the substrate blind side 15. Such initial spring-loaded locking engagement of the latch jaws 78 with the substrate blind side can be tactile-detected by the tool operator, but this initial spring-loaded locking force is insufficient to preclude withdrawal of the latch jaws 78 by pulling the tapered trailing end faces against the blind side edge of the substrate access opening 16.

Figure 9:
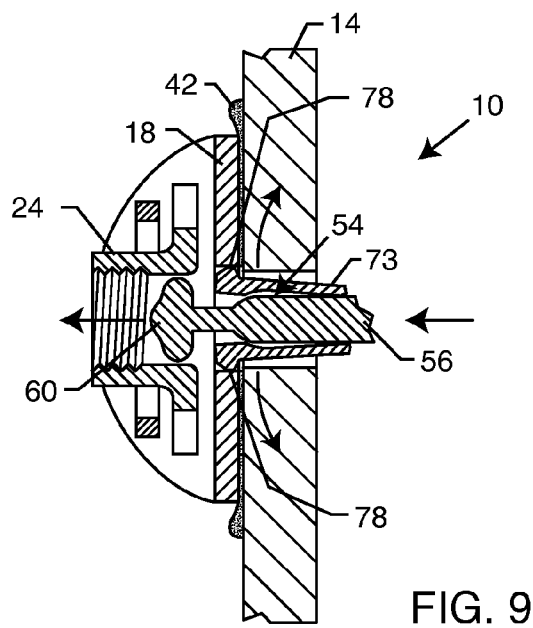
FIG. 9 is a fragmented vertical sectional view similar to FIG. 8, and depicting actuation of the tester unit for secure locking engagement with the substrate, and for applying a selected test force to the nutplate bonded to the substrate.
Figure 10:
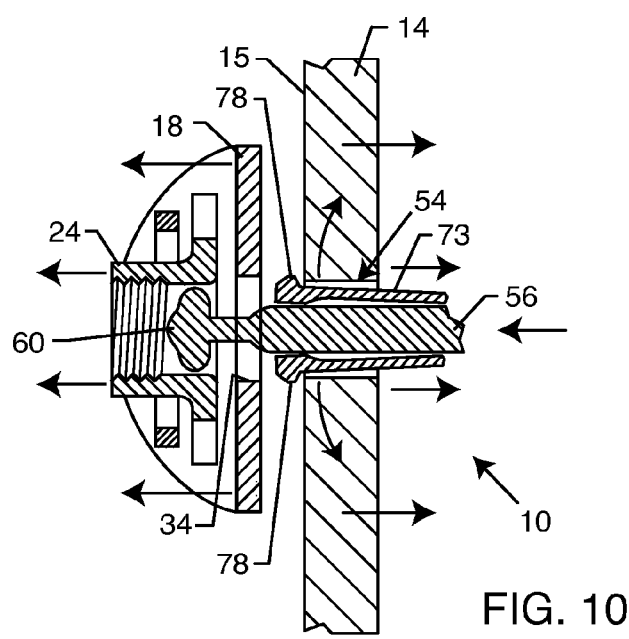
FIG. 10 is a fragmented vertical sectional view similar to FIGS. 8-9, and illustrating separation of the nutplate from the substrate thereby indicating inadequate bond strength attachment.

For normal use, with the latch jaws 78 springably engaged with the substrate blind side, the trigger lever 64 is depressed for initiating pneumatic advance movement of the pusher pin 56 relative to the reaction head 54. During this movement as depicted in FIG. 9, the cam surface 76 on the pin shank engages cam follower surfaces 82 on the latch arms 73 for positively forcing radial expansion of the latch arms 73 and the latch jaws 78 thereon, thereby positively and securely locking the latch jaws 78 against the substrate blind side 15. Further advance displacement of the pusher pin 56 moves the radially enlarged tip or cap 60 defined at the distal or free end thereof into engagement with the threaded nut 24, as by pressed engagement against the internal threads therein, to apply the test force of predetermined magnitude. As previously noted, in the event of an inadequate bond strength attachment of the nutplate 12 to the substrate blind side 15, the nutplate base 18 will separate from the substrate in response to the applied test force (as viewed in FIG. 10), thereby indicating a need for a replacement nutplate. Conversely, in the presence of adequate bond strength attachment, the nutplate base 18 will remain affixed to the substrate blind side.

Upon release of the trigger lever 64, the drive cylinder unit 66 is designed for reverse displacement to retract the pusher pin 56 relative to the reaction head 54. This displaces the cam surface 76 on the pin shank rearwardly relative to the cam follower surfaces 82 on the latch arms 73, and thereby releases the latch jaws 78 from positive locked engagement with the substrate. Instead, the latch jaws 78 remain engaged with the substrate by the comparatively small spring-loading applied by the latch arms 73, whereupon the tool tip 52 can be pulled manually from the substrate access opening 16. FIG. 1 shows a retraction spring 84 for drawing the pusher pin rearwardly upon trigger lever release, although persons skilled in the art will appreciate that a pneumatically driven retraction mechanism may be used.

FIGS. 11-17 illustrate one alternative preferred form of the invention, wherein components corresponding in structure and function with those shown and described in the embodiment of FIGS. 1 and 8-10 are identified by common reference numerals increased by 100. In general, the embodiment depicted in FIGS. 11-17 is directed to a modified tester unit 110 having a reaction head 154 and an actuator member 156 wherein the reaction head 154 is adapted for forward and reverse drive displacement relative to the actuator member 156 for applying a selected test force to a nutplate 12 or the like bonded onto a blind side 15 of a substrate 14.

Figure 11:
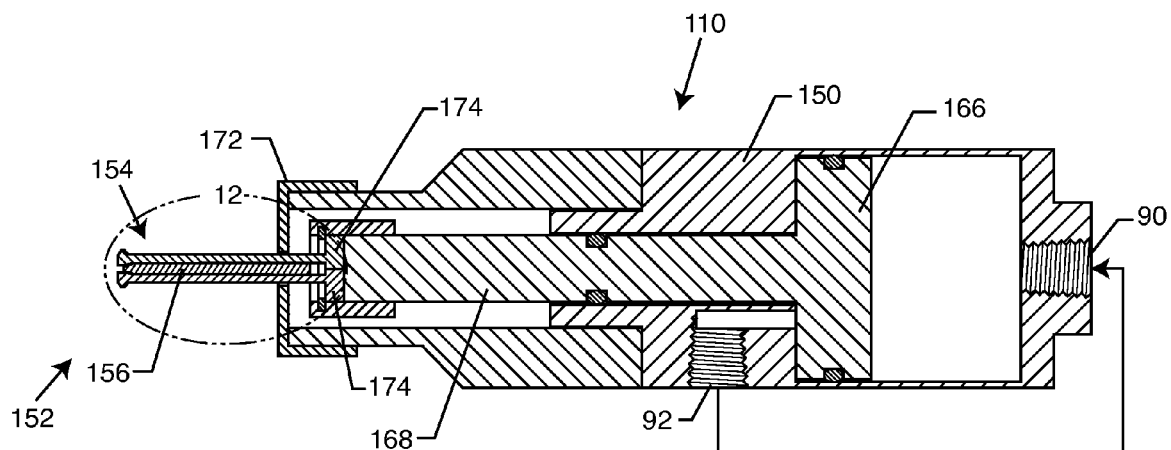
FIG. 11 is an enlarged vertical sectional view depicting a nutplate bond strength tester unit constructed in accordance with one alternative preferred form of the invention.
Figure 12:
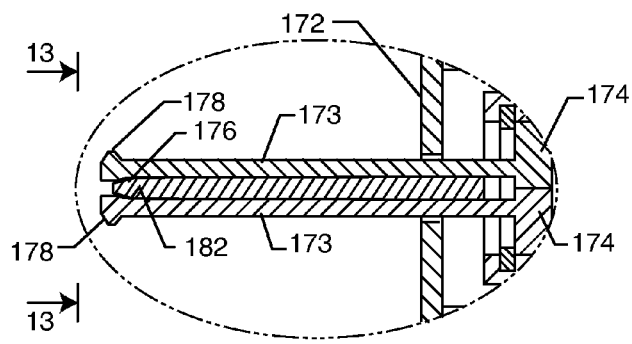
FIG. 12 is an enlarged fragmented vertical sectional view corresponding generally with the encircled region 12 of FIG. 11.
Figure 13:
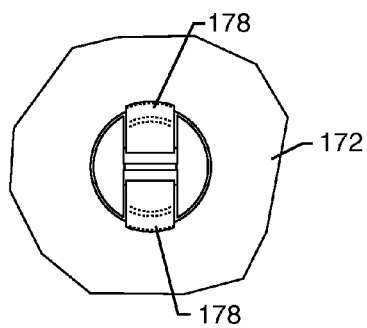
FIG. 13 is a front end elevation view of the tester unit of the tester unit taken generally on the line 13-13 of FIG. 12.
Figure 14:
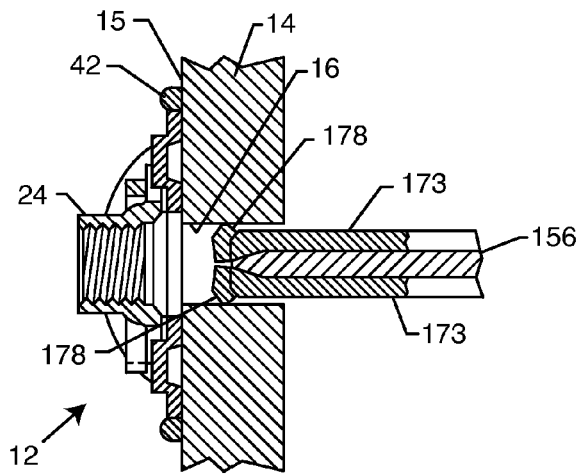
FIG. 14 is a fragmented vertical sectional view similar to FIGS. 8-10, but depicting insertion of the tool tip of the tester unit of FIG. 11 into a substrate access opening for testing bond strength of a nutplate mounted onto the substrate blind side.

More particularly, as shown in FIGS. 11-12, the modified tester unit 110 comprises a tool body 150 having a reciprocally driven ram 168 adapted for forward-drive or reverse-drive displacement in response to pneumatic or hydraulic driven movement of a drive cylinder unit 166. A control 164 is provided for coupling a suitable pressure fluid source to a first fitting 90 for forward-drive displacement of the ram 168, and to a second fitting 92 for reverse-drive ram displacement. Persons skilled in the art will recognize that supply of fluid under pressure to one of the fittings 90, 92 is accompanied by coupling the other of said fittings to a suitable exhaust port. The control 164 may comprise a suitable trigger-type element for manual actuation by a tool operator.

The tester unit 110 includes a tool tip 152 comprising the reaction head 154 and the actuator member 156. Similar to the previously described embodiment, the reaction head comprises a pair of elongated latch arms 173 having enlarged base ends 174 supported at a distal end of the ram 168 for at least slight pivoting movement. The latch arms 173 protrude forwardly from a front or nose end 172 of the tool body 150, and terminate at distal ends defined by a pair of latch jaws 178.

The actuator member 156 comprises an elongated pusher pin or the like mounted slidably and coaxially within the latch arms 173. As viewed best in FIGS. 12-13, this pusher pin 156 defines a tapered cam surface 176 for engaging matingly shaped cam follower surfaces 182 formed on the interior surfaces of the latch arms 173. The pusher pin 156 also has a lateral width dimension extending laterally beyond the latch jaws 178 (FIG. 13), wherein this width dimension is selected for engaging and pushing against the bond-mounted nutplate, as by engaging the internal threads within the nut 24.

Figure 15:
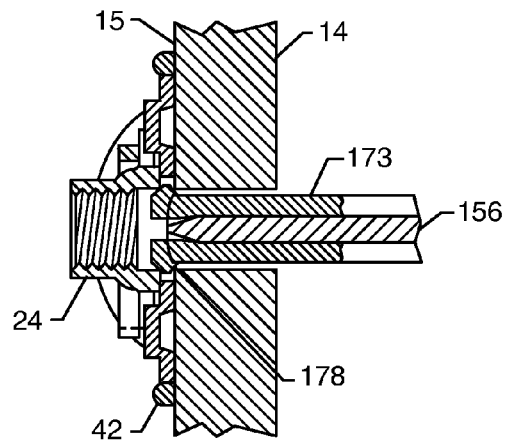
FIG. 15 is a fragmented vertical sectional view similar to FIG. 14, and depicting initial latched or locked engagement of the tester unit tool tip with the substrate.
Figure 16:
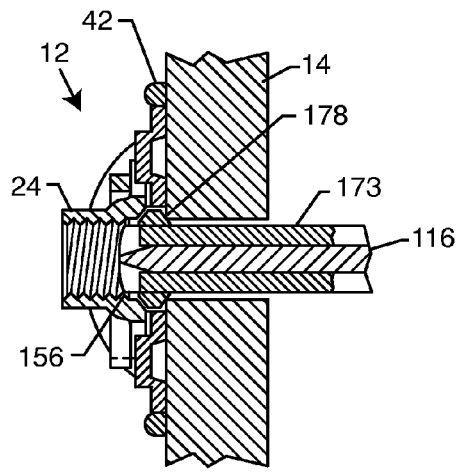
FIG. 16 is a fragmented vertical sectional view similar to FIG. 15, and illustrating actuation of the tester unit for secure locking engagement with the substrate, and for applying a selected test force to the nutplate bonded to the substrate.
Figure 17:
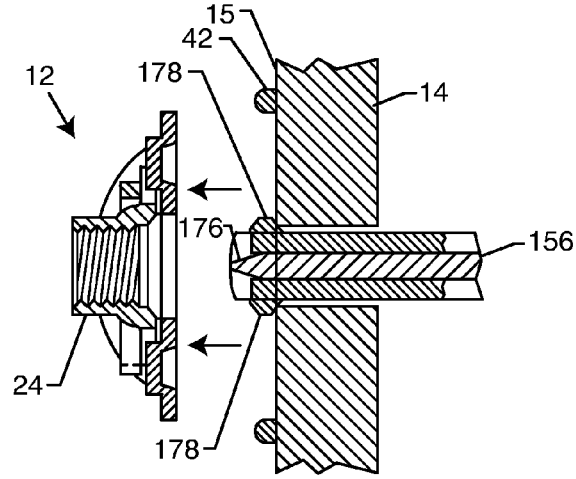
FIG. 17 is a fragmented vertical sectional view similar to FIGS. 14-16, and illustrating separation of the nutplate from the substrate thereby indicating inadequate bond strength attachment.

In operation, the tool tip 152 is inserted into a substrate access opening 16 (FIG. 14) for slidably fitting the latch jaws 178 in initial locked or latched engagement with the blind side 15 of the substrate (FIG. 15). As described in connection with the prior embodiment, the latch arms 173 have sufficient inherent spring characteristics for springably engaging the latch jaws 178 with the substrate in a manner that can be tactile-sensed by the tool operator. When this initial latched condition is achieved, the control 164 is suitably manipulated to retract the latch jaws 178 relative to the pusher pin 156 mounted slidably therein, as viewed in FIG. 16, resulting is relative advancement of the pusher pin for expanding the latch jaws 178 into positive locked engagement with the substrate followed promptly by displacing the pusher pin into pushing engagement with the nutplate bonded onto the substrate blind side. If the nutplate assembly 12 is bonded onto the substrate with sufficient bond strength, application of the predetermined test force by the pusher pin 156 will not result in nutplate dislocation. Conversely, if the insufficient bond strength is present, the pusher pin 156 will separate the nutplate 12 from the substrate (FIG. 17) thereby indicating a need for a replacement nutplate affixed with proper bond strength.

Following the test force application, the control 164 is suitably manipulated for advancing the latch jaws 178 relative to the pusher pin 156, thereby effectively retracting the pusher pin back into the latch arms 173 and thereby releasing the latch jaws 178 from positive locked engagement with the substrate. In this condition, the tool operator can withdraw the tool tip 152 from the substrate access opening, and thereafter use the tool 150 for testing bond strength attachment of a nutplate associated with a different access opening.

Although various embodiments and alternatives have been described in detail for purposes of illustration, various further modifications may be made without departing from the scope and spirit of the invention. Accordingly, no limitation on the invention is intended by way of the foregoing description and accompanying drawings, except as set forth in the appended claims.

What is claimed is:

1. A bond strength tester unit for testing the bond strength of an attachment component adhesively mounted onto a substrate, said tester unit comprising:
   a tool body carrying a radially expansible reaction head and an actuator member for movement one relative to the other, said reaction head being adapted for engagement with the substrate by slide-fit reception through an access opening formed in the substrate and for radial expansion to engage a blind side of the substrate upon passage of said latch jaws through the substrate access opening, and said actuator member being adapted for engagement with the attachment component when said reaction head engages the blind side of the substrate; and
   a drive unit for displacing one of said reaction head and said actuator member relative to the other for applying a test force of predetermined magnitude to the attachment component.

2. The bond strength tester unit of claim 1 wherein said drive unit reciprocally displaces said actuator member relative to said reaction head.

3. The bond strength tester unit of claim 1 wherein said drive unit reciprocally displaces said reaction head relative to said actuator member.

4. The bond strength tester unit of claim 1 wherein said drive unit comprises a fluid-driven cylinder unit.

5. The bond strength tester unit of claim 4 wherein said cylinder unit comprises a ram responsive to a fluid under pressure for movement in a first direction for displacing one of said reaction head and said actuator member relative to the other to apply said test force of predetermined magnitude to the attachment component.

6. The bond strength tester unit of claim 5 wherein said cylinder unit further comprises spring means for normally urging said ram in a second direction opposite to said first direction.

7. The bond strength tester unit of claim 1 wherein said reaction head comprises a plurality of radially movable latch jaws carried at the ends of a corresponding plurality of latch arms, and wherein said actuator member comprises a pusher pin including an enlarged cap carried at the end of an elongated shank and adapted for engagement with the attachment component, said pin shank being disposed substantially coaxially with respect to said latch arms.

8. The bond strength tester unit of claim 7 wherein said latch jaws have a size for slide-fit reception through an access opening formed in the substrate, and further wherein said latch arms springably urge said latch jaws radially outwardly for engaging a blind side of the substrate upon passage of said latch jaws through the substrate access opening.

9. The bond strength tester unit of claim 7 wherein said latch arms and said pin shank cooperatively defines cam surfaces for radially expanding said latch jaws upon relative displacement of said one of said reaction head and said actuator member relative to the other for applying said test force of predetermined magnitude to the attachment component.

10. A bond strength tester unit for testing the bond strength of an attachment component adhesively mounted onto a substrate, said tester unit comprising:
    a tool body carrying a reaction head including a plurality of radially movable latch jaws carried at the ends of a corresponding plurality of latch arms, and a pusher pin including an enlarged cap carried at the end of an elongated shank, said pin shank being disposed substantially coaxially with respect to said latch arms;
    said latch jaws having a size for slide-fit reception through an access opening formed in the substrate and for engaging a blind side of the substrate upon passage of said latch jaws through the substrate access opening;

said pin cap being positioned to engage the attachment component when said latch jaws are engaged with a blind side of the substrate; and a drive unit for displacing one of said reaction head and said pusher pin relative to the other for applying a test force of predetermined magnitude to the attachment component.

11. The bond strength tester unit of claim 10 wherein said latch arms springably urge said latch jaws radially outwardly for engaging a blind side of the substrate.

12. The bond strength tester unit of claim 10 wherein said latch arms and said pin shank cooperatively defines cam surfaces for radially expanding said latch jaws upon relative displacement of said one of said reaction head and said pusher pin relative to the other for applying said test force of predetermined magnitude to the attachment component.

13. The bond strength tester unit of claim 10 wherein said drive unit reciprocally displaces said pusher pin relative to said reaction head.

14. The bond strength tester unit of claim 10 wherein said drive unit reciprocally displaces said reaction head relative to said pusher pin.

15. A bond strength tester unit for testing the bond strength of an attachment component adhesively mounted onto a blind side of a substrate in a position in substantial alignment with an access opening formed in the substrate, said tester unit comprising:

a tool body carrying a reaction head including a plurality of radially movable latch jaws carried at the ends of a corresponding plurality of latch arms, and a pusher pin including an enlarged cap carried at the end of an elongated shank, said pin shank being disposed substantially coaxially with respect to said latch arms;

said latch jaws have a size for slide-fit reception through an access opening formed in the substrate and for engaging a blind side of the substrate upon passage of said latch jaws through the substrate access opening;

said pin cap being positioned to engage the attachment component when said latch jaws are engaged with a blind side of the substrate; and a drive unit for displacing one of said reaction head and said pusher pin relative to the other for applying a test force of predetermined magnitude to the attachment component, said latch arms and said pin shank cooperatively defining cam surfaces for radially expanding said latch jaws upon relative displacement of said one of said reaction head and said pusher pin relative to the other whereby said latch jaws engage a blind side of the substrate while said pusher pin applies said test force of predetermined magnitude to the attachment component.

16. The bond strength tester unit of claim 15 wherein the attachment component comprises a nutplate.

17. The bond strength tester unit of claim 15 wherein said latch arms springably urge said latch jaws radially outwardly for engaging a blind side of the substrate.

18. A bond strength tester unit for testing the bond strength of an attachment component adhesively mounted onto a substrate, said tester unit comprising:

a tool body carrying a reaction head and an actuator member for movement one relative to the other, said reaction head being adapted for engagement with the substrate, and said actuator member being adapted for engagement with the attachment component; and a drive unit comprising a fluid-driven cylinder unit having a ram responsive to a fluid under pressure for movement in a first direction for displacing one of said reaction head and said actuator member relative to the other for applying a test force of predetermined magnitude to the attachment component, and spring means for normally urging said ram in a second direction opposite to said first direction.

* * * * *